United States Patent
Okamoto et al.

(10) Patent No.: US 10,168,142 B2
(45) Date of Patent: Jan. 1, 2019

(54) OPTICAL CHARACTERISTIC MEASURING APPARATUS AND OPTICAL CHARACTERISTIC MEASURING METHOD

(71) Applicant: Otsuka Electronics Co., Ltd., Osaka (JP)

(72) Inventors: Sota Okamoto, Kyoto (JP); Yuki Sasaki, Konan (JP); Seon Heum Na, Yongin-si (KR)

(73) Assignee: OTSUKA ELECTRONICS CO., LTD., Osaka (JP)

( * ) Notice: Subject to any disclaimer, the term of this patent is extended or adjusted under 35 U.S.C. 154(b) by 0 days.

(21) Appl. No.: 15/845,899

(22) Filed: Dec. 18, 2017

(65) Prior Publication Data
US 2018/0172431 A1    Jun. 21, 2018

(30) Foreign Application Priority Data
Dec. 19, 2016    (JP) .................................. 2016-245796

(51) Int. Cl.
*G01J 3/28*    (2006.01)
*G01B 11/06*    (2006.01)

(52) U.S. Cl.
CPC ........ *G01B 11/0625* (2013.01); *G01J 3/2803* (2013.01)

(58) Field of Classification Search
CPC ........ G01J 3/02; G01J 3/10; G01J 3/28; G01J 3/2803; G01J 3/2823
USPC .......................................................... 356/326
See application file for complete search history.

(56) References Cited

U.S. PATENT DOCUMENTS

2005/0105103 A1\* 5/2005 Schietinger ........... B24B 37/013
356/630
2008/0285026 A1    11/2008 Okawauchi et al.

FOREIGN PATENT DOCUMENTS

JP    2008-286583 A    11/2008
JP    2010-002327 A    1/2010

\* cited by examiner

*Primary Examiner* — Md M Rahman
(74) *Attorney, Agent, or Firm* — Baker & Hostetler LLP

(57) ABSTRACT

An optical characteristic measuring apparatus includes an optical system, a detector, and an analysis unit. The optical system collects detection light incident from a sample. The detector spectrally disperses the detection light in plural times to generate plural pieces of detection data, the plural pieces of detection data indicating their respective spectra of detection light incident from the sample to the optical system with an optical distance between the sample and the optical system being different from each other. The analysis unit analyzes the spectrum indicated by the detection data to measure a predetermined optical characteristic of the sample. The analysis unit specifies a piece of the detection data to be used for measuring the optical characteristic based on intensity of the detection light in the plural pieces of detection data, and measures the optical characteristic based on the specified piece of the detection data.

9 Claims, 9 Drawing Sheets

REFLECTANCE DATA

ANALYSIS DATA

ESTIMATE REFLECTANCE DATA

200
OPTICAL CHARACTERISTIC MEASURING APPARATUS AND OPTICAL CHARACTERISTIC MEASURING METHOD

BACKGROUND

1. Technical Field

The present invention relates to an optical characteristic measuring apparatus and an optical characteristic measuring method for measuring optical characteristics such as a film thickness of a sample.

2. Related Art

Conventionally, an optical interference method using the phase of light is known as a method for measuring optical characteristics such as a film thickness (for example, JP 2008-286583 A and JP 2010-002327 A). In the optical interference method, a spectrum of light reflected by the sample to be measured is measured with a spectrometer, and the optical characteristics of the sample are measured by analyzing data of the spectrum.

JP 2008-286583 A discloses an optical characteristic measuring apparatus that improves precision in measurement of optical characteristics by facilitating focusing on a sample (object to be measured). In JP 2008-286583 A, spectrum measurement of reflected light is performed after a user changes the positional relationship between the sample and an objective lens with reference to the state of a reflected image shown by a display or a controller performs focusing using an automatic focusing technique. The optical characteristic measuring apparatus of JP 2008-286583 A has a mechanism for focusing, such as a camera and an observation-purpose light source and employs a complex optical system incorporating optical components for using this mechanism.

SUMMARY

In a conventional method of measuring optical characteristics, it is necessary to perform focusing at the time of spectrum measurement. Thus, it takes time to measure the optical characteristics, and by providing a mechanism for focusing, the configuration of the apparatus becomes large-scale.

An object of the present invention is to provide an optical characteristic measuring apparatus and an optical characteristic measuring method which can facilitate measurement of optical characteristics of a sample based on light from a sample.

An optical characteristic measuring apparatus according to an aspect of the present invention includes an optical system, a detector, and an analysis unit. The optical system collects detection light incident from a sample. The detector spectrally disperses the detection light in plural times to generate plural pieces of detection data, the plural pieces of detection data indicating their respective spectra of detection light incident from the sample to the optical system with an optical distance between the sample and the optical system being different from each other. The analysis unit analyzes the spectrum indicated by the detection data to measure a predetermined optical characteristic of the sample. The analysis unit specifies a piece of the detection data to be used for measuring the optical characteristic based on intensity of the detection light in the plural pieces of detection data, and measures the optical characteristic based on the specified piece of the detection data.

An optical characteristic measuring method according to an aspect of the present invention includes collecting detection light incident from a sample through an optical system. The present method includes spectrally dispersing the detection light in plural times to generate plural pieces of detection data by a detector, the plural pieces of detection data indicating their respective spectra of detection light incident from the sample to the optical system with an optical distance between the sample and the optical system being different from each other The present method includes specifying a piece of the detection data to be used for measuring a predetermined optical characteristic of the sample based on intensity of the detection light in the plural pieces of detection data by an analysis unit. The present method includes analyzing the spectrum indicated by the specified piece of the detection data to measure the optical characteristic by the analysis unit.

According to the optical characteristic measuring apparatus and optical characteristic measuring method according to the present invention, a piece of detection data to be used for measurement of an optical characteristic is specified from plural pieces of detection data having different optical distances from each other. This allows it easier to measure an optical characteristic of a sample based on light from the sample.

DETAILED DESCRIPTION OF EMBODIMENT

Figure 1:
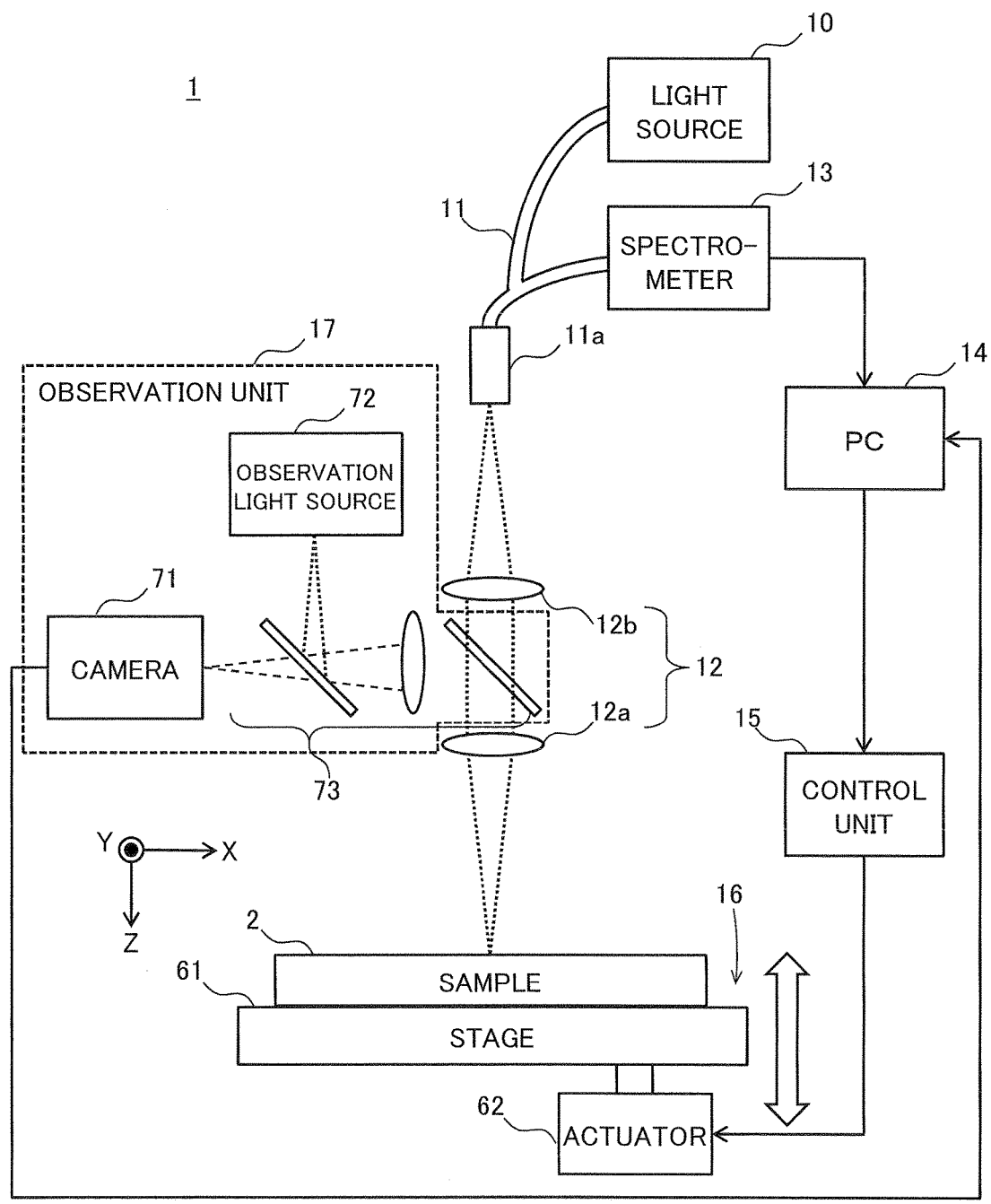
FIG. 1 is a block diagram showing a configuration of an optical characteristic measuring apparatus according to a first embodiment.

Hereinafter, embodiments of the present invention will be described with reference to the accompanying drawings. In each of the following embodiments, the same constituent elements are denoted by the same reference numerals.

First Embodiment

An optical characteristic measuring apparatus and an optical characteristic measuring method according to the first embodiment will be described below.

1. Configuration

The configuration of the optical characteristic measuring apparatus according to the present embodiment will be described with reference to FIG. 1. FIG. 1 is a block diagram showing the configuration of the optical characteristic measuring apparatus 1 according to the first embodiment.

The optical characteristic measuring apparatus 1 according to the present embodiment is an apparatus that performs optical analysis on light incident from a sample 2 to be measured and measures optical characteristics such as a film thickness of the sample 2. As shown in FIG. 1, the optical characteristic measuring apparatus 1 includes a light source 10, an optical fiber 11, an objective optical system 12, a spectrometer 13, a personal computer (PC) 14, a control unit 15, a driving unit 16, and an observation unit 17.

Examples of the sample 2 include various semiconductor substrates on which thin films such as single layer films and multilayer films are formed, glass substrates, and film members. In the present embodiment, the sample 2 is arranged on a horizontal plane (stage 61) in the driving unit 16 of the optical characteristic measuring apparatus 1. Hereinafter, two directions orthogonal to each other in the horizontal plane of the sample 2 are defined as an "X direction" and a "Y direction", respectively, and the normal direction of the horizontal plane is defined as a "Z direction".

The light source 10 emits irradiation light for irradiating the sample 2. The irradiation light emitted from the light source 10 is, for example, white light and has a continuous wavelength spectrum (continuous spectrum) within a wavelength band corresponding to the optical characteristics of the sample 2 to be measured. The light source 10 may be constituted by various light sources such as an incandescent lamp, a light emitting diode (LED), a deuterium lamp, a xenon lamp, and a halogen lamp.

The optical fiber 11 is constituted by, for example, a Y-type fiber having one probe end 11a and two branch ends. The probe end 11a is optically connected to the objective optical system 12, one of the branch ends is connected to the light source 10, and the other of the branch ends is connected to the spectrometer 13. The optical fiber 11 is an example of a coupling optical system that optically couples the light source 10 and the objective optical system 12 and optically couples the objective optical system 12 and the spectrometer 13. The coupling optical system is not limited to the optical fiber 11, and may be an optical system in which, for example, various optical elements are arranged.

The objective optical system 12 is an optical system that collects and guides light emitted to the sample and light incident from the sample 2 in the optical characteristic measuring apparatus 1. The objective optical system 12 in the present embodiment includes a first lens 12a facing the sample 2, a second lens 12b disposed between the first lens 12a and the probe end 11a of the optical fiber 11, and the like. As shown in FIG. 1, the lenses 12a and 12b are arranged so that the optical axis of the objective optical system 12 faces in the Z direction, and perform focusing and collimation. The objective optical system 12 has an inherent depth of field which is defined by the optical characteristics and the like of the first and second lenses 12a and 12b.

The spectrometer 13 spectrally disperses (i.e. spectrally resolves) incident light to detect a wavelength spectrum of light. The spectrometer 13 is an example of a detector in the present embodiment. The spectrometer 13 is constituted by, for example, a multichannel spectrometer. The spectrometer 13 includes a spectroscopic optical system including a slit and a grating or the like, a detection element such as a CCD image sensor having a light receiving surface, and an internal memory. The detection element may be constituted by a photodiode array or the like.

In the multichannel spectrometer 13, the incident light is guided to the grating through the slit, diffracted by the grating, and incident on the detection element. As a result, the detection element receives diffracted light in a region different for each wavelength on the light receiving surface and realizes a self-scanning operation of simultaneously detecting intensity of light of plural wavelength components (for example, 512 components). The spectrometer 13 buffers detection data based on detection results of the detection element in the internal memory and generates detection data of light received at a predetermined cycle (for example, 1 to 5 milliseconds). An example of the detection data (reflectance data) will be described later.

The PC 14 includes, for example, a CPU that realizes a predetermined function in cooperation with software, an internal memory such as a flash memory. The internal memory stores, for example, data received from the spectrometer 13, a program for executing the optical characteristic measuring method according to the present embodiment. The PC 14 reads data and programs stored in the internal memory and performs various arithmetic processing to realize various functions.

For example, the PC 14 receives the detection data from the spectrometer 13 and performs predetermined data processing on the detection data, thereby analyzing the optical characteristics. The PC 14 is an example of an analysis unit in the present embodiment. Further, in the present embodiment, the PC 14 performs various control by performing data communication with each unit in the optical characteristic measuring apparatus 1.

The control unit 15 is a control device that controls driving of the driving unit 16 based on an instruction from the PC 14. The control unit 15 includes, for example, a microcomputer and a communication interface. The control function of the control unit 15 may be realized in the PC 14.

The driving unit 16 includes the stage 61 having a horizontal plane on which the sample 2 is disposed, and an actuator 62 that drives the stage 61 to move. For example, in the driving unit 16, the stage 61 is configured to be movable in three directions of X, Y, and Z axes respectively. By moving in the X and Y directions, it becomes easy to measure the film thickness of the sample 2 at various horizontal positions. The driving unit 16 may be configured such that the stage 61 can only move in a single direction of the Z axis.

The observation unit 17 is a module for observing the principal surface of the sample 2 and the like in the optical characteristic measuring apparatus 1 and includes a camera 71, an observation light source 72, an observation optical system 73, and the like.

The camera 71 includes an image pickup element such as a charge coupled device (CCD) or a complementary metal oxide semiconductor (CMOS) imaging element. The camera 71 generates image data indicating a picked-up (captured) image and outputs the captured image data to the PC 14.

The observation light source 72 is a light source for illuminating the sample 2 when the camera 71 captures an image of the sample 2, and is constituted by a white LED or the like.

The observation optical system 73 is an optical system that guides light emitted from the observation light source 72 to the sample 2 and light incident on the camera from the sample 2, and includes a beam splitter and a lens. In the present embodiment, as shown in FIG. 1, a part of the observation optical system 73 is incorporated inside the objective optical system 12. Thereby, it is also possible to observe the state of the light incident on the spectrometer 13 in the objective optical system 12 with the observation unit 17.

In the optical characteristic measuring apparatus 1 according to the present embodiment, the observation unit 17 may be omitted, particularly when there is no need to observe the sample 2. According to the optical characteristic measuring method according to the present embodiment, it is possible to measure the film thickness and the like of the sample 2 without using the observation unit 17.

2. Operation

The operation of the optical characteristic measuring apparatus 1 configured as described above will be described below.

2-1. Overview of Operation

The overview of the operation of the optical characteristic measuring apparatus 1 will be described with reference to FIGS. 1 and 2.

In the optical characteristic measuring apparatus (FIG. 1), the light source 10 emits irradiation light. The irradiation light enters the objective optical system 12 via the optical fiber 11. As shown in FIG. 1, the irradiation light is collimated by the second lens 12b of the objective optical system 12, collected by the first lens 12a, and radiated to the sample 2 disposed on the stage 61.

In the sample 2, the irradiation light is reflected by each of two principal surfaces having an interval corresponding to the film thickness of the sample 2 therebetween. The light reflected on each principal surface enters the objective optical system 12 while interfering in accordance with the interval corresponding to the film thickness of the sample 2.

In the optical characteristic measuring apparatus 1, the reflected light from the sample 2 is collimated at the first lens 12a of the objective optical system 12, collected at the second lens 12b, and enters to the spectrometer 13 via the optical fiber 11. The spectrometer 13 generates reflectance data as detection data indicating a wavelength spectrum of light including reflected light from the sample 2. The reflectance data generated by the spectrometer 13 will be described with reference to FIG. 2.

Figure 2:
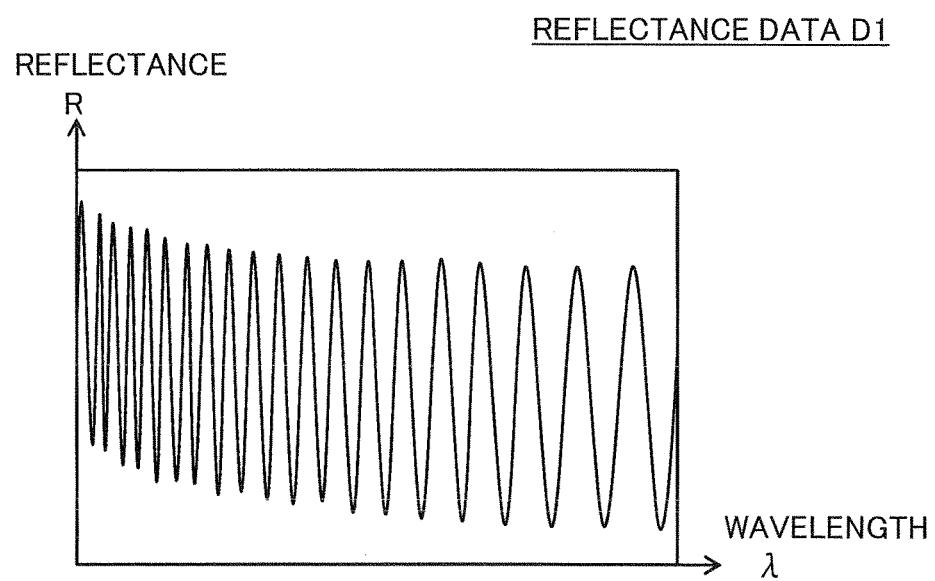
FIG. 2 is a diagram for explaining reflectance data in the optical characteristic measuring apparatus.

FIG. 2 is a diagram for explaining reflectance data D1 in the optical characteristic measuring apparatus 1. Reflectance data D1 indicates a reflectance spectrum which is a wavelength spectrum of the reflected light detected by the spectrometer 13. As shown in FIG. 2, the reflectance spectrum is represented by reflectance R of various wavelength λ components in the detected reflected light. In the reflectance data D1, the oscillation of the reflectance R in the reflectance spectrum shown in FIG. 2 is caused by the interference of the reflected light by the interval corresponding to the film thickness of the sample 2.

Returning to FIG. 1, the PC 14 in the optical characteristic measuring apparatus 1 calculates the film thickness of the sample 2 by analyzing the reflectance data D1 generated by the spectrometer 13. Various known methods such as a nonlinear least squares method, a fast Fourier transform (FFT) method, a peak valley method can be applied in the film thickness calculation process by the PC 14 (see JP 2010-002327 A).

2-2. Findings of Inventors

In a method of measuring the film thickness, acquiring the reflectance data D1 with high accuracy allows the film thickness to be measured accurately. From this fact, in a conventional method, focusing is performed between a spectrometer and a sample to ensure the accuracy of the acquired reflectance data. Meanwhile, the inventors of the present invention have achieved a method of obtaining highly accurate reflectance data without performing particular focusing as a result of earnest study. Hereinafter, an experiment from which the inventors have gained findings to reach such an idea will be described with reference to FIG. 3.

Figure 3:
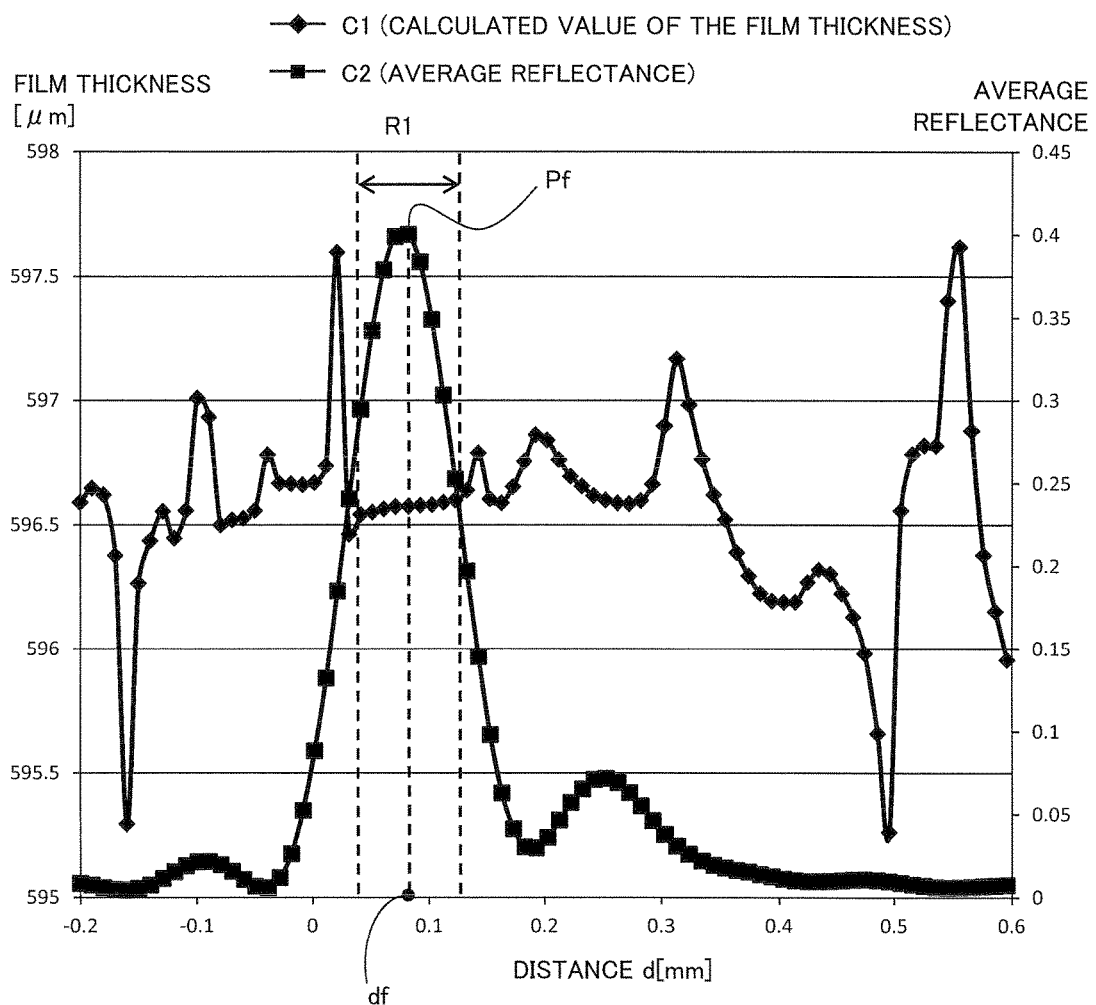
FIG. 3 is a graph showing results of an experiment relating to the optical characteristic measuring method.

FIG. 3 is a graph showing results of an experiment conducted by the inventors. In this experiment in the optical characteristic measuring apparatus 1, while changing distance d from the objective optical system 12 to the sample 2 (that is, the Z position), reflected light entering the spectrometer 13 from the sample 2 at each distance d was detected, and reflectance data D1 of each detection result was generated.

In the graph of FIG. 3, the horizontal axis indicates the distance d from a predetermined position to the sample 2 in the Z direction of the optical characteristic measuring apparatus 1. A curve C1 indicates values of the film thickness calculated by using a predetermined arithmetic expression for the reflectance data D1 based on the reflected light detected at each distance d (see the vertical axis on the left side of FIG. 3).

A curve C2 indicates an average reflectance in reflectance data D1 at each distance d (see the vertical axis on the right side of FIG. 3). The average reflectance is an average over multitude of reflectance in a reflectance spectrum (the reflectance R of each wavelength λ) in one piece of reflectance data D1 and corresponds to the intensity (magnitude) of the detected reflected light. The two curves C1 and C2 indicate calculated values of the film thickness and the average reflectance based on the same piece of reflectance data D1 for each distance d.

According to the curve C1 of FIG. 3, the variation in the calculated value of the film thickness is remarkably larger outside a region R1 than inside the region R1. The region R1 is a region corresponding to depth of field of the objective optical system 12. Further, the curve C2 has a peak Pf in the region R1 of the depth of field. A position df of the peak in the region R1 is considered to be a true focus position within the range of the depth of field because the intensity of the detected reflected light is at the maximum at the position df.

In the region R1 of the depth of field shown in FIG. 3, the curve C1 of the calculated values of the film thickness is stable but inclined. Thus, the calculated value of the film thickness at the true focus position df is different from the calculated values of the film thickness at other positions. According to a typical focus technique such as a contrast method, it is difficult to obtain the reflectance data D1 at the true focus position df by performing focusing inside the region R1 of the depth of field, since every position in the region R1 of the depth of field is on focus state. To address this, the inventors of the present invention has paid attention to the curve C2 in this experiment and has found that the reflectance data D1 at the true focus position df can be easily specified by checking the peak Pf of the average reflectance.

2-3. Details of Operation

Based on the findings of the inventors described above, the optical characteristic measuring apparatus 1 according to the present embodiment preforms scanning to continuously detect the reflected light by the spectrometer 13 while moving the sample 2 in the Z direction within a predetermined range to generate plural pieces of reflectance data D1 in which distances d to the sample 2 are different from each other. Then, the PC 14 selects a piece of reflectance data D1 to be used for film thickness measurement based on the average reflectance of each of the plural pieces of generated reflectance data D1. Thus, the optical characteristic measuring apparatus 1 can easily measure the film thickness without performing focusing.

Hereinafter, details of the operation of the optical characteristic measuring apparatus 1 according to the present embodiment will be described with reference to FIGS. 4, 5, and 6.

Figure 4:
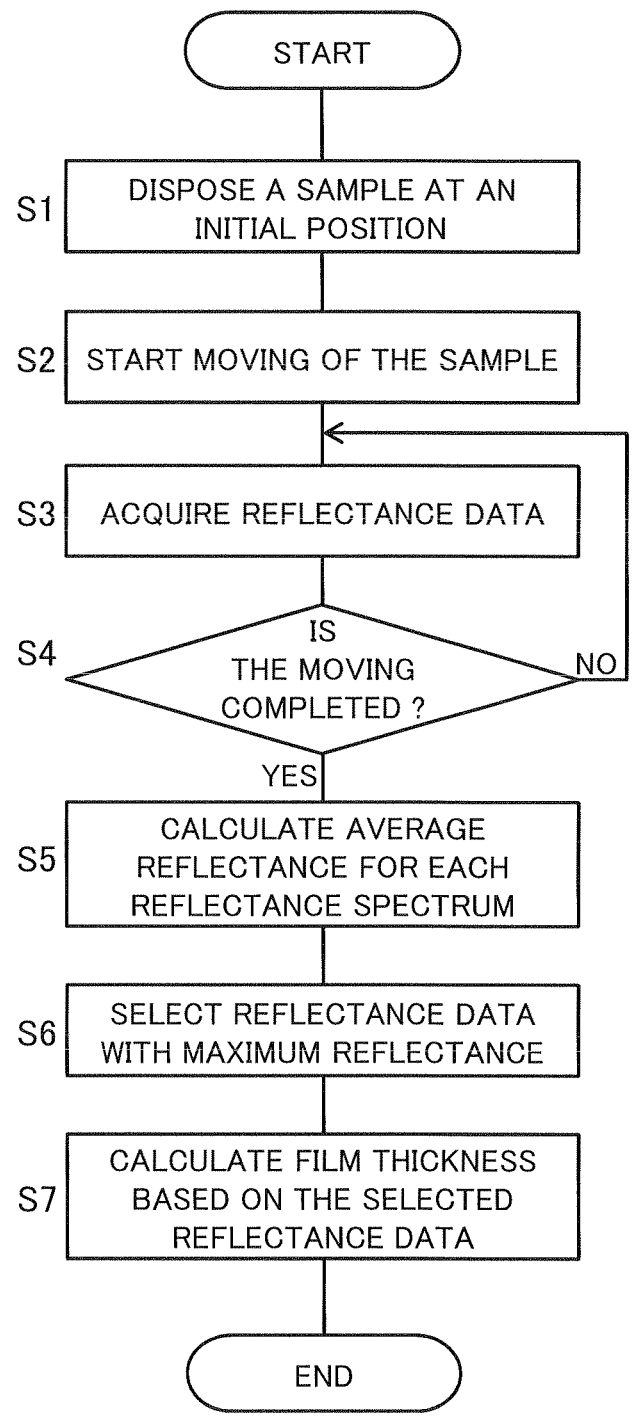
FIG. 4 is a flowchart showing an operation of the optical characteristic measuring apparatus according to the first embodiment.

FIG. 4 is a flowchart showing the operation of the optical characteristic measuring apparatus 1 according to the present embodiment. FIG. 5 is a diagram for explaining the operation of the optical characteristic measuring apparatus 1. FIGS. 6A and 6B are diagrams for explaining a method of calculating the film thickness by the optical characteristic measuring apparatus 1.

The flowchart in FIG. 4 is executed by the PC 14 in the optical characteristic measuring apparatus 1. This flowchart is started with the light source 10 radiating the irradiation light.

Figure 5:
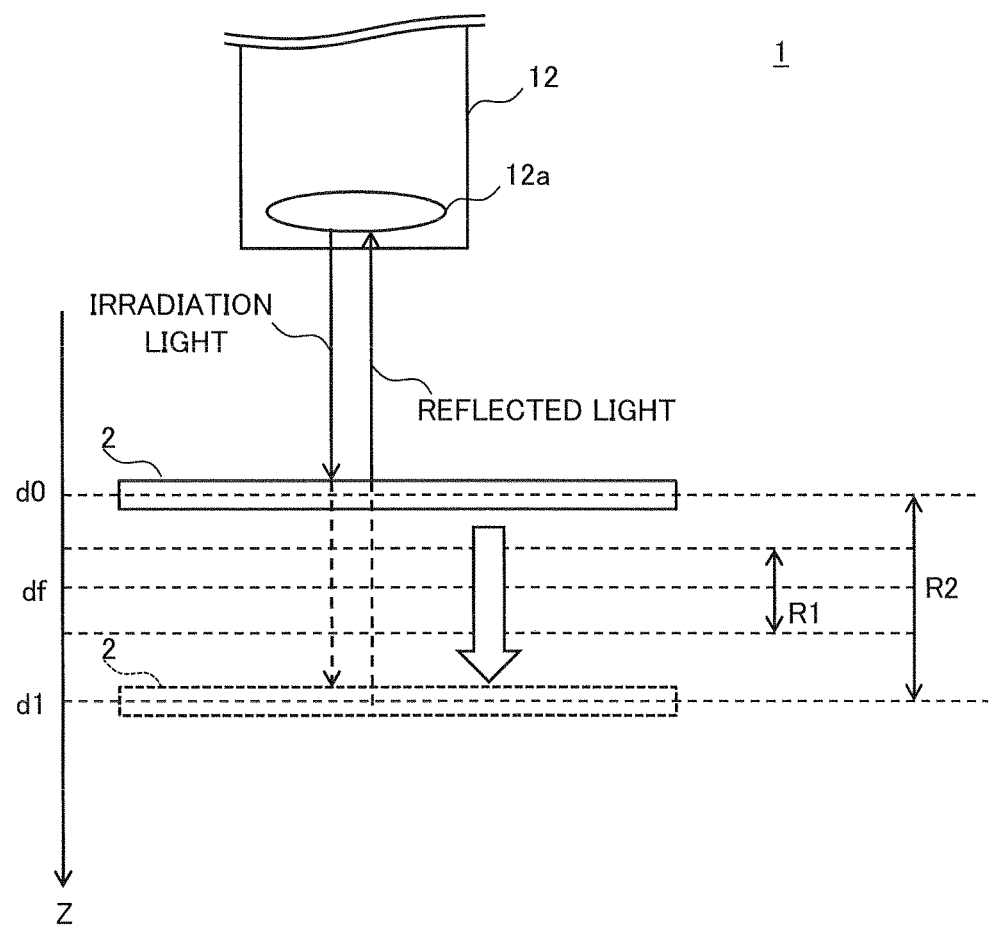
FIG. 5 is a diagram for explaining the operation of the optical characteristic measuring apparatus according to the first embodiment.
Figure 6A:
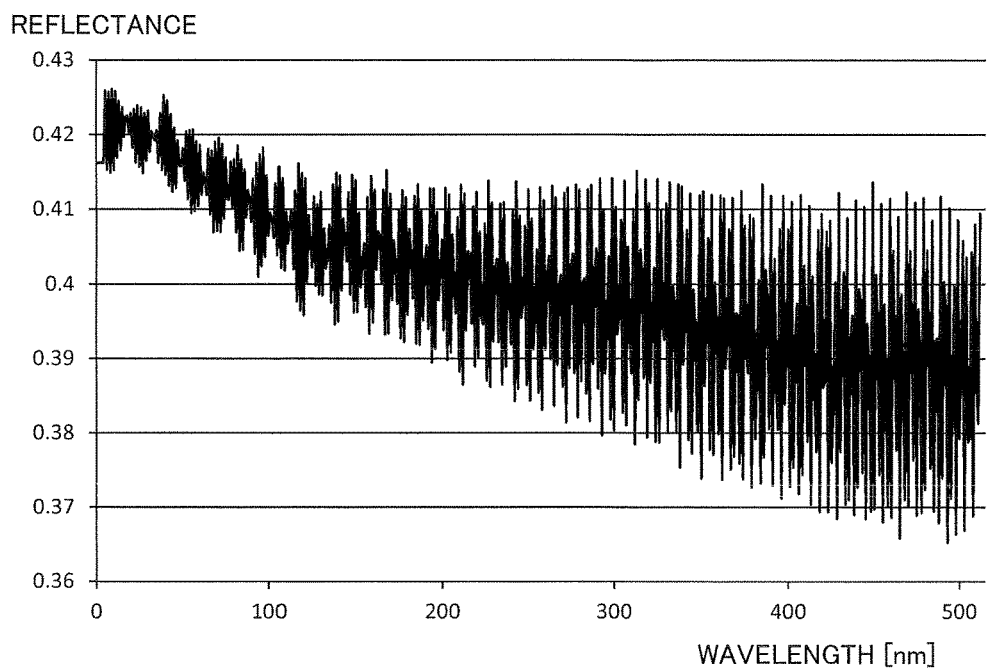
FIGS. 6A and 6B are diagrams for explaining a method of calculating a film thickness by the optical characteristic measuring apparatus.
Figure 6B:
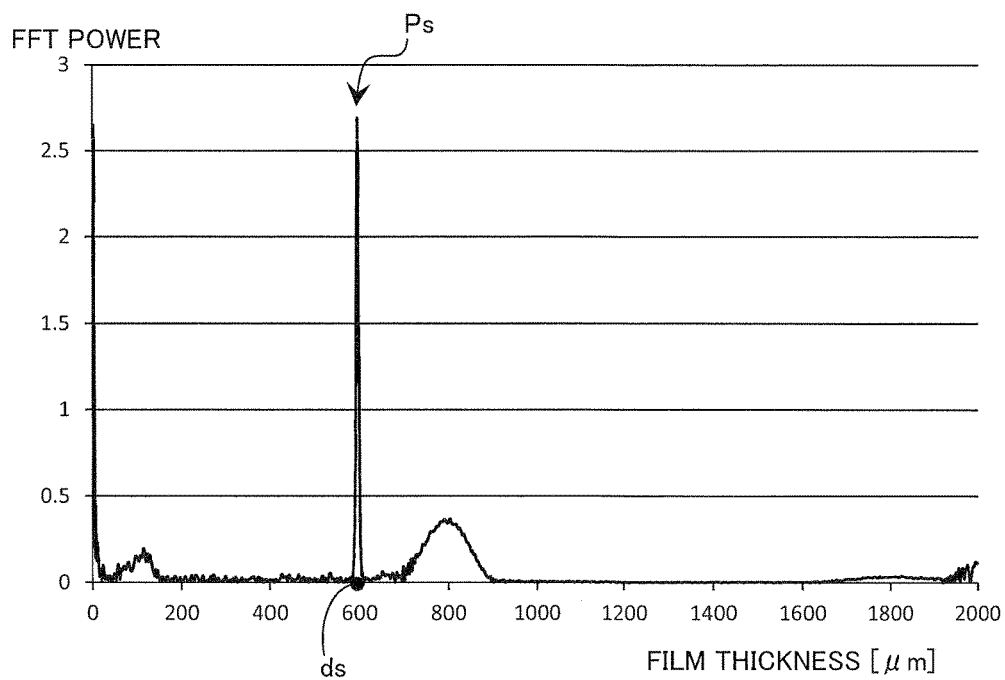

First, the PC 14 controls the Z position of the stage 61 in the driving unit 16 via the control unit 15 to move the sample 2 on the stage 61 to an initial position d0 (FIG. 5) in the Z direction as shown in FIG. 5 (S1). The initial position d0 is a position to start scanning of the sample 2 by moving the sample 2 while acquiring the reflectance data D1. Scanning in the optical characteristic measuring apparatus 1 will be described with reference to FIG. 5.

FIG. 5 shows a scan region R2 in the optical characteristic measuring apparatus 1. The scan region R2 is a region where the sample 2 moves in steps S2 to S4 (while scanning). As shown in FIG. 5, one end of the scan region R2 is the initial position d0, and the other end of the scan region R2 is an end position d1 at which the scanning is ended. That is, the sample 2 is moved from the initial position d0 to the end position d1. In the present embodiment, the scan region R2 is set to a predetermined range (for example, a 1 mm section) including the region R1 of the depth of field of the objective optical system 12. As a result, the true focus position df is also included in the scan region R2.

Returning to FIG. 4, next, the PC 14 transmits an instruction for start of movement to the control unit 15 to start movement of the stage 61 (FIG. 1), on which the sample 2 is disposed, in the scan region R2 (S2). Upon receiving the instruction for start of movement, the control unit 15 controls the actuator 62 of the driving unit 16 to start the movement of the stage 61 in the Z direction.

After starting the movement of the sample 2, the spectrometer 13 detects reflected light of the irradiation light in the sample 2 at a predetermined cycle (for example, 1 millisecond). The spectrometer 13 generates the reflectance data D1 of the detection results and sequentially outputs the reflectance data D1 to the PC 14. The PC 14 acquires the reflectance data D1 from the spectrometer 13 (S3).

At this time, the control unit 15 moves the stage at a predetermined speed (for example, 0.5 mm/second) without synchronizing the movement timing of the stage 61 with the movement timing of the spectrometer 13 in particular. Then, the control unit 15 transmits notification to the PC 14 when the stage 61 reaches the end position d1. The operation cycle of the spectrometer 13 and the movement speed of the stage 61 are set as appropriate from the viewpoint of, for example, the number of times the reflectance data D1 is obtained in the scan region R2, or tolerance to the true focus position df.

Based on the notification from the control unit 15, the PC 14 determines whether or not the movement of the sample 2 is completed (S4). The PC 14 repeats the processing of step S3 and subsequent steps until receiving the notification indicative of the end of movement from the control unit 15 (NO in S4). Thereby, plural pieces of reflectance data D1 are acquired, including reflectance data based on the reflected light at the timing when the sample 2 passes through the true focus position df in the scan region R2. The plural pieces of reflectance data D1 are respectively detected in a state where the distances d from the objective optical system 12 to the sample 2 are different from each other.

When it is determined that the movement of the sample 2 is completed (YES in S4), the PC 14 calculates an average reflectance by averaging the multitude of reflectance in the reflection spectrum for each piece of the plural pieces of acquired reflectance data D1 (S5). Specifically, the PC 14 calculates the average value by integrating the reflectance R for each wavelength λ component in one piece of reflectance data D1, and performs similar calculation for each of the plural pieces of reflectance data D1.

Next, based on the calculated average reflectance, the PC 14 selects one piece of reflectance data having the maximum average reflectance from the plural pieces of acquired reflectance data D1 (S6). The processing of step S6 is processing for specifying a piece of reflectance data to be used for calculating the film thickness from the plural pieces of acquired reflectance data D1.

Next, based on the selected piece of reflectance data, the PC 14 analyzes the reflectance spectrum indicated by the reflectance data by, for example, the FFT method to calculate the film thickness of the sample 2 (S7). The processing of step S7 will be described in detail with reference to FIGS. 6A and 6B.

FIG. 6A shows an example of a piece of reflectance data selected in step S6. FIG. 6B illustrates analysis data indicating analysis results for the piece of reflectance data of FIG. 6A.

FIG. 6A exemplifies a piece of reflectance data obtained at the position df of the peak Pf of the average reflectance (curve C2) shown in FIG. 3. When a piece of reflectance data as shown in FIG. 6A is selected in step S6, the PC 14 converts the wavelength λ of the wavelength spectrum in the selected piece of reflectance data into a wave number and performs FFT on the converted data. At this time, the PC 14 uses various preset parameters such as the refractive index of the sample 2.

By the above analysis processing, the analysis data of FIG. 6B is obtained from the detection data of FIG. 6A. According to FIG. 6B, a peak Ps corresponding to an oscillation characteristic in the wavelength region in FIG. 6A is obtained in a film thickness unit. The PC 14 calculates the position ds of the peak Ps in such a film thickness unit as the film thickness of the sample 2 (S7).

The PC 14 calculates the film thickness (S7), and thereby the processing according to the flowchart of FIG. 4 is ended.

According to the above processing, plural pieces of reflectance data D1 are acquired (S2 to S4) while moving the sample 2 in the scan region R2 including the true focus position df, and the film thickness is obtained by using a piece of reflectance data having the largest average reflectance (S5 to S7). Thus, it is possible to easily measure the film thickness without performing complex control, such as focusing, or synchronizing the operation timing of the spectrometer 13 with the movement timing of the stage 61. Further, the piece of highly accurate reflectance data considered to have been obtained in the vicinity of the most true focus position df among the plural pieces of reflectance data D1 is specified (S6), and thus the film thickness can be measured with high accuracy.

Although in the above description, the control unit 15 does not particularly synchronize the movement timing of the stage 61 with the operation timing of the spectrometer 13 in steps S3 and S4, the timings may be synchronized. For example, the stage 61 may be moved stepwise, or the Z position of the stage 61 at the timing of acquiring the reflectance data may be associated with the reflectance data.

In the above description, the PC 14 is performed the calculation of the average reflectance of each piece of reflectance data D1 after proceeding to "YES" in step S4. However, the present invention is not limited to this, and for example, the average reflectance may be sequentially calculated from the reflectance data D1 starting from the piece of reflectance data D1 acquired in step S3.

3. Summary

As described above, the optical characteristic measuring apparatus 1 according to the present embodiment includes the objective optical system 12, the spectrometer 13, and the PC 14. The objective optical system 12 collects reflected light of an example of detection light incident from the sample 2. The spectrometer 13 spectrally disperses the reflected light of the sample 2 in plural times to generate plural pieces of reflectance data D1. The plural pieces of reflectance data D1 are exemplary plural pieces of detection data indicating their respective spectra of the reflected light incident from the sample 2 to the objective optical system 12 with an optical distance between the sample 2 and the objective optical system 12 being different from each other. The PC 14 analyzes the spectrum indicated by the reflectance data D1 to measure an optical characteristic such as the film thickness of the sample 2. Based on the intensity (average reflectance) of the detection light in the plural pieces of reflectance data D1, the PC 14 specifies the piece of detection data to be used for the measurement of optical characteristics, and measures the optical characteristic based on the specified piece of detection data.

According to the optical characteristic measuring apparatus 1 described above, a piece of detection data to be used for measurement of optical characteristics is specified from plural pieces of reflectance data D1 whose optical distances are different from each other. This makes it easy to measure the optical characteristics of the sample 2 based on the light from the sample 2.

The intensity of the detection light (reflected light) for specifying the piece of detection data is not limited to the average reflectance over a reflectance spectrum of the reflectance data D1. For example, a summed value of the reflectance R over the reflectance spectrum, or an average value or a summed value of the reflectance R in a wavelength band of a part of the reflectance spectrum may be used as the intensity of the detection light described above.

In the present embodiment, the optical characteristic measuring apparatus 1 further includes the light source 10 that irradiates the sample 2 with irradiation light. The detection light includes reflected light of the irradiation light on the sample 2. The PC 14 measures the film thickness of the sample 2 as an optical characteristic. This makes it easier to measure the film thickness of the sample 2 based on the reflected light from the sample 2.

In the present embodiment, the spectrometer 13 generates plural pieces of detection data based on the detection light incident during a period in which the optical distance between the sample 2 and the objective optical system 12 varies within a predetermined range. The predetermined range is the scan region R2 including the focus position df of the objective optical system 12. As a result, a piece of detection data while the sample 2 is passing through the focus position df in the scan region R2 is obtained, and the optical characteristics of the sample 2 can be accurately measured by specifying such a piece of detection data.

In the present embodiment, the PC 14 selects a piece of detection data corresponding to the largest intensity of the detection light among the plural detection data to specify the piece of detection data for measuring optical characteristics. As a result, the piece of detection data with the highest accuracy among the plural detection data can be used for measuring the optical characteristics.

In the present embodiment, the optical characteristic measuring apparatus 1 further includes the driving unit 16. The driving unit 16 moves the sample 2 to vary the optical distance between the sample 2 and the objective optical system 12. Instead of or in addition to moving the sample 2, the optical characteristic measuring apparatus 1 may be equipped with a driving unit including an actuator or the like for moving the objective optical system 12.

In the present embodiment, the spectrometer 13 serving as a detector is constituted by, for example, a multichannel spectrometer. The spectrometer 13 is not limited to a multichannel type, and various spectrometers may be used.

Further, the optical characteristic measuring method according to the present embodiment includes collecting the detection light incident from the sample 2 via the objective optical system 12. This method includes steps of the spectrometer 13 spectroscopically dividing the detection light of the sample 2 incident through the objective optical system 12 by the spectrometer 13 plural times in a state where the optical distances between the sample 2 and the objective optical system 12 are different from each other and generating plural pieces of detection data indicating respective spectra of the detection light. This method includes specifying the piece of detection data to be used for measuring a predetermined optical characteristic of the sample 2 based on the intensity of the detection light in the plural pieces of detection data. This method includes analyzing a spectrum indicated by the specified piece of detection data and measuring an optical characteristic.

According to the optical characteristic measuring method described above, it is easy to measure the optical characteristics of the sample 2 based on the light from the sample 2.

Second Embodiment

In the first embodiment, a piece of reflectance data in the vicinity of the true focus position df is selected from the plural pieces of reflectance data D1. In the second embodiment, data estimation of reflectance data at the true focus position df is performed based on the plural pieces of reflectance data D1. Hereinafter, the optical characteristic measuring apparatus 1 according to the present embodiment will be described with reference to FIGS. 7 and 8.

Figure 7:
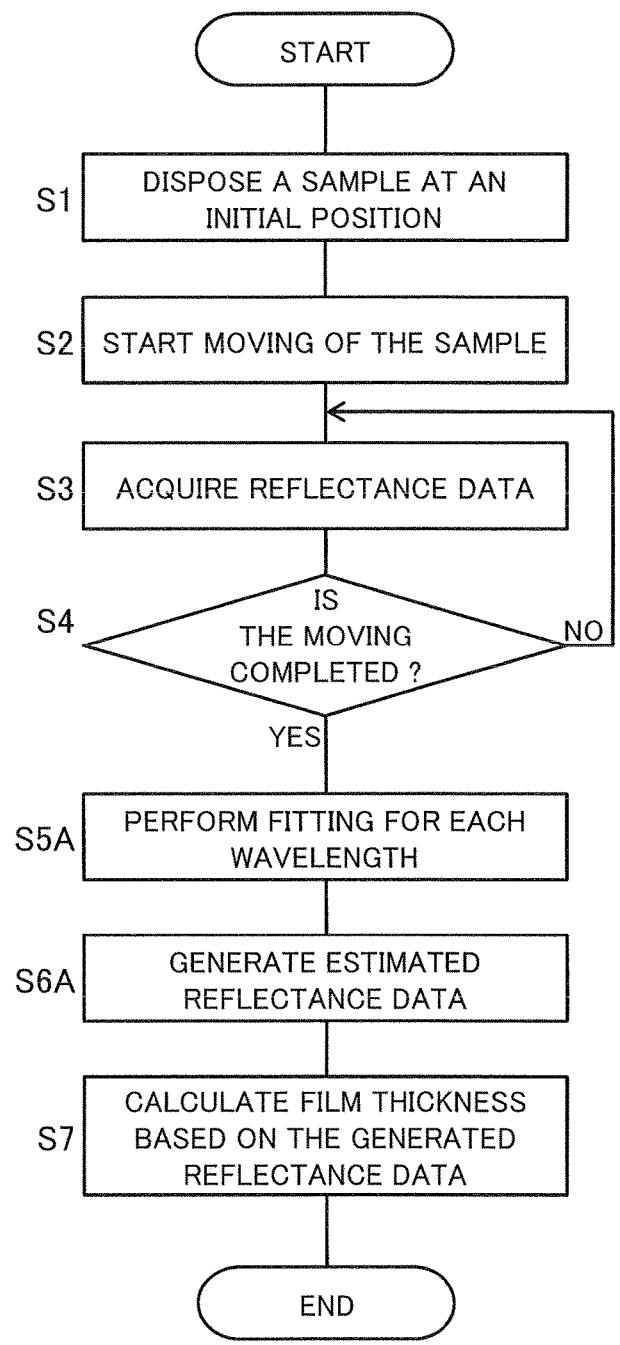
FIG. 7 is a flowchart showing an operation of an optical characteristic measuring apparatus according to a second embodiment.

FIG. 7 is a flowchart showing the operation of the optical characteristic measuring apparatus 1 according to the second embodiment. FIG. 8 is a diagram for explaining the optical characteristic measuring apparatus 1 according to the second embodiment.

The optical characteristic measuring apparatus 1 according to the present embodiment, whose configuration is similar to the optical characteristic measuring apparatus 1 according to the first embodiment, performs the operation shown in the flowchart of FIG. 7. In the flowchart of FIG. 7, the PC 14 of the optical characteristic measuring apparatus 1 executes processing (steps S5A and S6A) for estimating reflectance data instead of the steps S5 and S6 of FIG. 4. Estimation of reflectance data will be described with reference to FIGS. 8A and 8B.

Figure 8A:
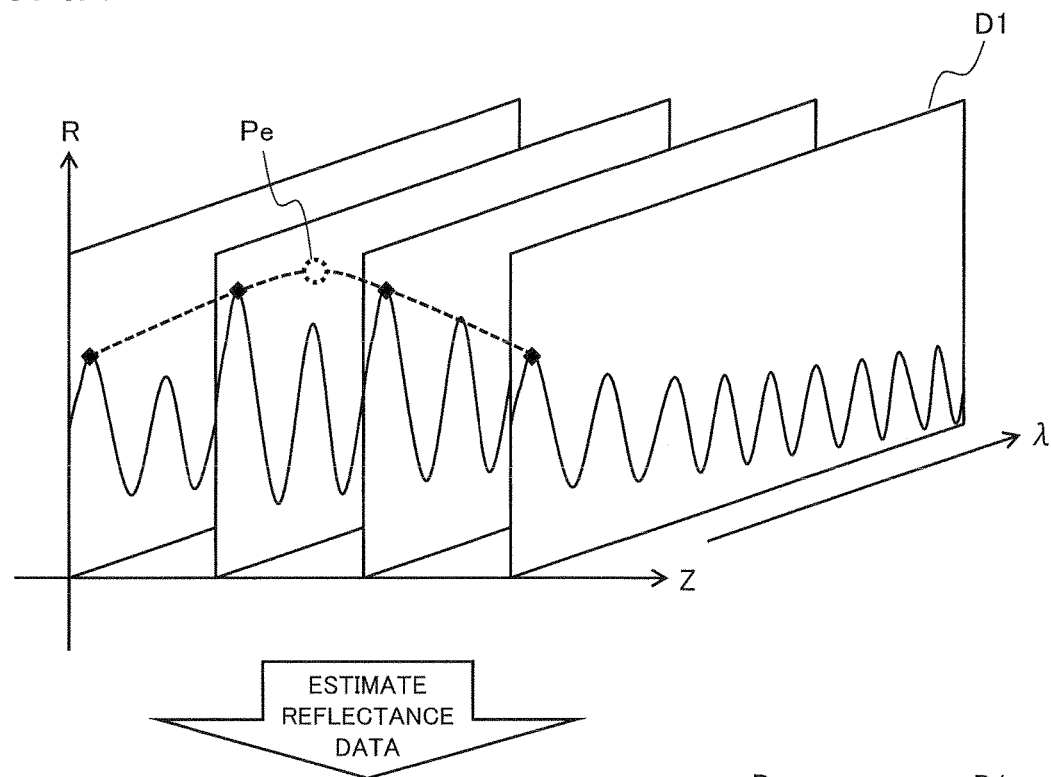
FIG. 8A and 8B are diagrams for explaining the optical characteristic measuring apparatus according to the second embodiment.

FIG. 8A shows plural pieces of reflectance data D1 acquired in steps S3 and S4 of FIG. 7. By arranging the plural pieces of reflectance data Dl in the order in which the plural pieces of reflectance data D1 are acquired in steps S3 and S4, it is possible to check the reflectance data D1 in the Z direction as shown in FIG. 8A. Therefore, in the present embodiment, in the case where, for example, the reflectance data D1 has not been obtained right above the true focus position df (see FIG. 3), the reflectance data at the true focus position df is estimated from the plural pieces of reflectance data D1 (see FIG. 8B).

Specifically, in the flowchart of FIG. 7, the PC 14 performs fitting for each wavelength λ component based on the plural pieces of reflectance data D1 acquired in steps S3 and S4 (step S5A).

In step S5A, the PC 14 extracts pieces of data of the same wavelength λ component from the plural pieces of reflectance data D1, and performs curve fitting in an RZ plane as shown in FIG. 8A. In this case, the intervals between pieces of data in the Z direction is set to be, for example, equal, and a predetermined functional form such as a quadratic function is used for curve fitting. By the processing of step S5A, a peak Pe as shown in FIG. 8A is detected in each wavelength λ component.

Figure 8B:
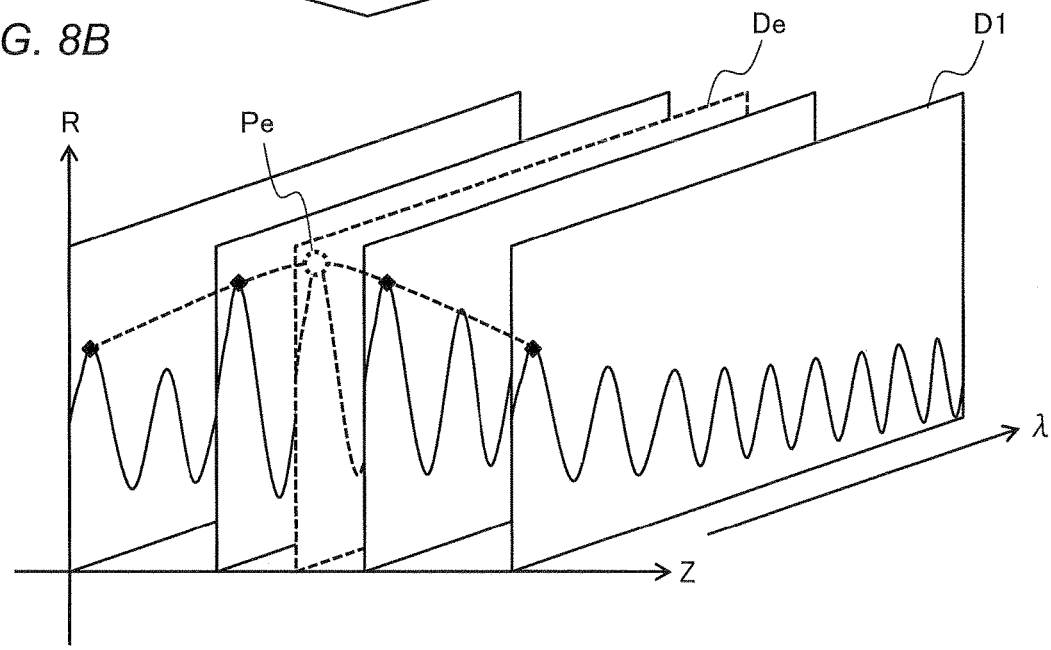

Next, based on the fitting result for each wavelength λ component, the PC 14 generates estimated reflectance data De as shown in FIG. 8B (S6A). For example, the PC 14 collects the peak Pe in each wavelength λ component and generates the estimated reflectance data De such that the estimated reflectance data De represents a wavelength spectrum corresponding to each peak Pe. Such estimated reflectance data De has a larger reflectance R than each of the pieces of detection data D1 from which the estimated reflectance data De is generated.

The PC 14 calculates the film thickness based on the generated estimated reflectance data De (S7).

According to the processing described above, the estimated reflectance data De based on the plural pieces of reflectance data D1 acquired in steps S3 and S4 is specified as detection data for measuring the optical characteristics such as film thickness.

In the above step S6A, when generating the estimated reflectance data De by collecting the peak Pe in each wavelength λ component, the Z position of the peak Pe of each wavelength λ component does not need to coincide. Even in such a case, it is possible to obtain the estimated reflectance data De with high accuracy by the fitting in step S5A.

Also, the method of generating the estimated reflectance data De in step S6A is not limited to the method described above. For example, the estimated reflectance data De may be generated so as to have a common Z position (corresponding to the true focus position df) over each wavelength λ component. For example, the PC 14 may determine the Z position by averaging the Z position of the peak Pe of each wavelength λ component or by referring to the peak Pe of a specific wavelength λ component in which λ has a predetermined value. Then, the PC 14 may collect data of the determined Z position from the fitting result of step S5A.

As described above, in the optical characteristic measuring apparatus 1 according to the present embodiment, the PC 14 generates estimated detection data (De) based on the plural pieces of detection data (D1) for measuring optical characteristics. The estimated detection data (De) has intensity of the detection light (reflectance R) larger than the intensity of detection light of each piece of detection data. As a result, a piece of highly accurate detection data can be specified and used for measurement of optical characteristics even if detection data has not been acquired right above the true focus position df.

Other Embodiments

In the first and second embodiments, the driving unit 16 is used, but the driving unit 16 does not need to be used. Such a modified embodiment will be described with reference to FIG. 9.

Figure 9:
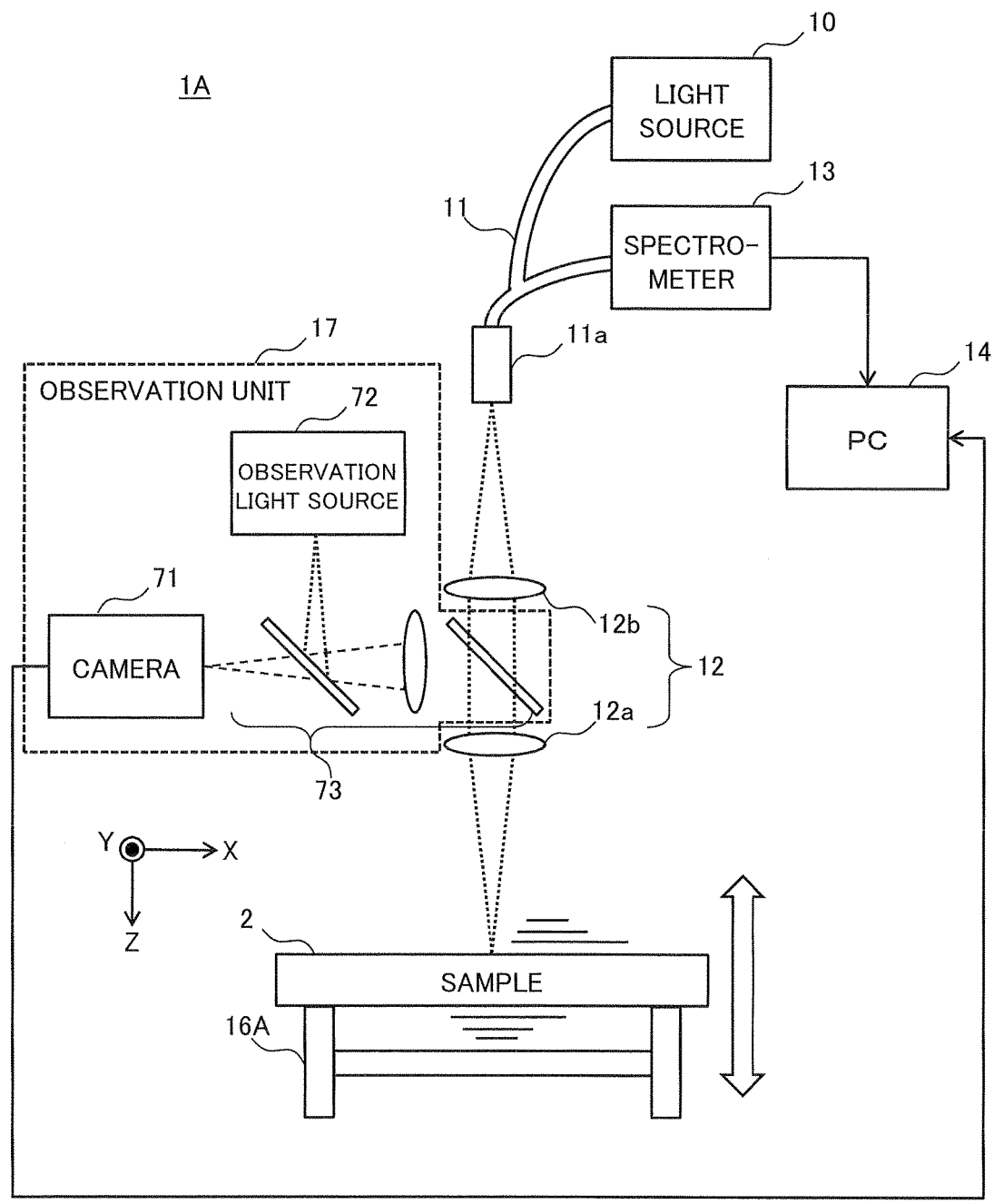
FIG. 9 is a block diagram showing a configuration of an optical characteristic measuring apparatus according to a modified embodiment.

FIG. 9 is a block diagram showing a configuration of an optical characteristic measuring apparatus 1A according to a modified embodiment. The optical characteristic measuring apparatus 1A according to the present modified embodiment has a configuration similar to the optical characteristic measuring apparatus 1 according to the first embodiment, and includes a supporting member 16A for supporting the sample 2 instead of the driving unit 16 and the control unit 15.

For example, for a sample 2 such as a large glass substrate, the sample 2 itself may vibrate naturally. In such a case, by detecting the plural pieces of reflectance data Dl with the spectrometer 13 during the period in which the sample 2 itself is vibrating, the optical characteristic measuring apparatus 1A can specify the piece of reflectance data suitable for measurement of the optical characteristics. In this case, the supporting member 16A is positioned such that, for example, the focus position df is included within the amplitude of vibration of the sample 2.

Further, even when the sample 2 is vibrating or not particularly vibrated, the spectrometer 13 in the optical characteristic measuring apparatus 1A may detect plural pieces of reflectance data D1 while manually moving the sample 2 or the objective optical system 12. Even when the manual movement is performed, a piece of reflectance data suitable for measurement of optical characteristics can be specified similarly to the case where driving is performed by the actuator 62 as in the first embodiment.

In the above embodiments, the film thickness is measured as an optical characteristic of the sample 2. However, an optical characteristic of a measurement target is not limited to the film thickness. The optical characteristic of the measurement target may be, for example, the color, refractive index, reflectance, or extinction coefficient of the sample 2, and may be a fluorescence characteristic such as a fluorescence spectrum or fluorescence energy. When measuring the fluorescence characteristic, the spectrometer 13 generates detection data representing a fluorescence spectrum.

In the case of measuring a fluorescence characteristic, for example, an excitation light source that emits excitation light is used as the light source 10 in the optical characteristic measuring apparatus 1. In addition, the sample 2 may be electrically excited to cause fluorescence emission, and in the case where the sample 2 self-emits light, the light source 10 may be omitted in the optical characteristic measuring apparatus 1.

In the above embodiments, the distance between the sample 2 and the objective optical system 12 is changed when generating plural pieces of detection data. However, the present invention is not limited to this. For example, the optical path length between the sample 2 and the objective optical system 12 may be changed by using various optical elements. When generating plural pieces of detection data each having different optical distance such as the distance or the optical path length between the sample 2 and the objective optical system 12, the optical characteristic measuring apparatus 1 can specify a piece of detection data suitable for measuring the optical characteristic.

The invention claimed is:

1. An optical characteristic measuring apparatus comprising:
    an optical system, having an optical axis and a focus position on the optical axis, configured to collect detection light incident from a sample;
    a detector configured to spectrally disperse the detection light in plural times to generate plural pieces of detection data, the plural pieces of detection data indicating their respective spectra of detection light incident from the sample to the optical system with an optical distance between the sample and the optical system being along the optical axis, wherein each optical distance is different from each other in a scanning range in which the sample passes through the focus position of the optical system; and
    a processor configured to analyze the spectrum indicated by the detection data to measure a predetermined optical characteristic of the sample,
    wherein the processor
    specifies a piece of the detection data for measuring the optical characteristic of the sample based on intensity of the detection light in the plural pieces of detection data each having different optical distances in the scanning range in which the sample passes through the focus position along the optical axis, and
    measures the optical characteristic based on the specified piece of the detection data.

2. The optical characteristic measuring apparatus according to claim 1, further comprising a light source configured to irradiate the sample with irradiation light,
    wherein the detection light includes reflected light of the irradiation light on the sample, and
    wherein the processor measures a film thickness of the sample as the optical characteristic.

3. The optical characteristic measuring apparatus according to claim 1, wherein the detector generates the plural pieces of detection data based on the detection light incident during a period in which the optical distance between the sample and the optical system varies within a predetermined range, and
    wherein the predetermined range includes the focus position of the optical system.

4. The optical characteristic measuring apparatus according to claim 1,
    wherein the processor selects a piece of detection data with maximum intensity of the detection light among the plural pieces of detection data to specify the selected piece of detection data for measuring the optical characteristic.

5. The optical characteristic measuring apparatus according to claims 1,
    wherein the processor generates estimated detection data based on the plural pieces of detection data to specify the estimated detection data for measuring the optical characteristic, the estimated detection data having intensity of the detection light larger than the intensity of the detection light in each piece of detection data.

6. The optical characteristic measuring apparatus according to claim 1, further comprising an actuator configured to move at least one of the sample and the optical system to vary the optical distance between the sample and the optical system.

7. The optical characteristic measuring apparatus according to claim 1, wherein the detector generates the plural pieces of detection data based on detection light incident during a period in which the sample naturally vibrates.

8. The optical characteristic measuring apparatus according to claim 1, wherein the detector is constituted by a multichannel spectrometer.

9. An optical characteristic measuring method comprising:
    collecting detection light incident from a sample through an optical system having an optical axis and a focus position on the optical axis;
    spectrally dispersing the detection light in plural times to generate plural pieces of detection data by a detector, the plural pieces of detection data indicating their respective spectra of detection light incident from the sample to the optical system with an optical distance between the sample and the optical system being along the optical axis, wherein each optical distance is different from each other in a scanning range in which the sample passes through the focus position of the optical system;
    specifying a piece of the detection data for measuring a predetermined optical characteristic of the sample based on intensity of the detection light in the plural pieces of detection data each having different optical distances in the scanning range in which the sample passes through the focus position along the optical axis by a processor; and
    analyzing the spectrum indicated by the specified piece of the detection data to measure the optical characteristic of the sample by the processor.

* * * * *